US012569834B2

(12) United States Patent
Okada et al.

(10) Patent No.: US 12,569,834 B2
(45) Date of Patent: Mar. 10, 2026

(54) UNIFORM-TYPE PLATINUM-LOADED ALUMINA CATALYST, METHOD OF PRODUCING SAME, AND METHOD OF USING SAME

(71) Applicant: Chiyoda Corporation, Yokohama (JP)

(72) Inventors: Yoshimi Okada, Yokohama (JP);
Kenichi Imagawa, Yokohama (JP);
Masashi Saito, Yokohama (JP); Kenta Fukudome, Yokohama (JP); Haruto Kobayashi, Yokohama (JP)

(73) Assignee: CHIYODA CORPORATION,
Kanagawa (JP)

( * ) Notice: Subject to any disclaimer, the term of this patent is extended or adjusted under 35 U.S.C. 154(b) by 243 days.

(21) Appl. No.: 17/918,591

(22) PCT Filed: Apr. 23, 2020

(86) PCT No.: PCT/JP2020/017563
§ 371 (c)(1),
(2) Date: Oct. 13, 2022

(87) PCT Pub. No.: WO2021/214954
PCT Pub. Date: Oct. 28, 2021

(65) Prior Publication Data
US 2023/0141512 A1      May 11, 2023

(51) Int. Cl.
*B01J 23/58*        (2006.01)
*B01J 21/04*        (2006.01)
(Continued)

(52) U.S. Cl.
CPC .............. *B01J 23/58* (2013.01); *B01J 21/04* (2013.01); *B01J 27/02* (2013.01); *B01J 35/397* (2024.01);
(Continued)

(58) Field of Classification Search
CPC .......... B01J 35/397; B01J 21/04; B01J 23/58; C01B 2203/107; C07C 2523/42; C07C 2521/04
See application file for complete search history.

(56) References Cited

U.S. PATENT DOCUMENTS 6,600,082 B2 *   7/2003  Le Peltier .............. B01J 23/626
                                                                585/629
9,623,403 B2     4/2017  Zhang et al.
(Continued)

FOREIGN PATENT DOCUMENTS

CN        106693993 A  *  5/2017  .............. B01J 27/02
CN        105268459 B      2/2018
(Continued)

OTHER PUBLICATIONS

Machine Translation of CN110882703A (Year: 2020).*
(Continued)

*Primary Examiner* — Ellen M Mcavoy
*Assistant Examiner* — Ming Cheung Po
(74) *Attorney, Agent, or Firm* — Armstrong Teasdale LLP

(57)             ABSTRACT

To provide a uniform-type platinum-loaded alumina catalyst demonstrating excellent performance in terms of catalyst life, a uniform-type platinum-loaded alumina catalyst includes: an alumina carrier; sulfur or a sulfur compound dispersed over an entire cross section of the alumina carrier; platinum dispersed and loaded over the entire cross section of the alumina carrier; one or more alkali metals selected from the group consisting of sodium, potassium, and calcium. Preferably, the content of platinum is 0.05 to 5.0 wt % calculated as elemental platinum. The content of the sulfur or the sulfur compound preferably is 0.15 to 5.0 wt %
(Continued)

(A)

(B)

calculated as elemental sulfur. The content of the alkali metal preferably is 0.1 to 5.0 wt % calculated as elemental alkali metal.

1 Claim, 1 Drawing Sheet

(51) Int. Cl.

| | | |
|---|---|---|
| *B01J 27/02* | (2006.01) | |
| *B01J 35/30* | (2024.01) | |
| *B01J 35/61* | (2024.01) | |
| *B01J 35/63* | (2024.01) | |
| *B01J 35/64* | (2024.01) | |
| *B01J 37/02* | (2006.01) | |
| *B01J 37/18* | (2006.01) | |
| *C07C 5/367* | (2006.01) | |

(52) U.S. Cl.
CPC ........... *B01J 35/615* (2024.01); *B01J 35/633* (2024.01); *B01J 35/647* (2024.01); *B01J 37/0201* (2013.01); *B01J 37/0236* (2013.01); *B01J 37/18* (2013.01); *C07C 5/367* (2013.01); *C07C 2521/04* (2013.01); *C07C 2523/58* (2013.01)

(56) References Cited

U.S. PATENT DOCUMENTS

| | | | | |
|---|---|---|---|---|
| 2009/0105511 | A1* | 4/2009 | Okada | ..................... B01J 21/04 502/223 |
| 2012/0065443 | A1* | 3/2012 | Mabande | ................ C07C 5/393 585/654 |
| 2021/0077894 | A1 | 3/2021 | Huang | |

FOREIGN PATENT DOCUMENTS

| | | | | | |
|---|---|---|---|---|---|
| CN | 110882703 | A | * | 3/2020 | ............. C07C 5/367 |
| EP | 1894626 | A1 | * | 3/2008 | ............ B01J 27/053 |
| JP | H0672005 | B2 | | 9/1994 | |
| JP | 2005211845 | A | | 8/2005 | |
| JP | 2006052110 | A | | 2/2006 | |
| JP | 2008050338 | A | | 3/2008 | |
| JP | 4142733 | B2 | | 9/2008 | |
| JP | 4652695 | B2 | | 3/2011 | |
| JP | 2012206909 | A | | 10/2012 | |
| WO | 2007125539 | A1 | | 11/2007 | |
| WO | 2019201706 | A1 | | 10/2019 | |

OTHER PUBLICATIONS

Machine translation of CN 106693993A (Year: 2017).*
Office Action for Australian Patent Application No. 2020443710 dated Nov. 29, 2023; 5 pp.
Extended European Search Report for EP Patent Application No. 20932604.0 dated Jan. 31, 2024; 8 pp.
Office Action for Taiwan Patent Application 110114570 dated Mar. 17, 2022; 9 pp.
International Search Report for Patent Application PCT/JP2020/017563 mailed Jun. 23, 2020; 3 pp.
Okada, Yoshimi, "H2 Storage and Transportation Technology by Organic Chemical Hydride Method and Future Prospects;" Energy and Resources, vol. 39, No. 3, 2018; pp. 168-173.
Okada, Yoshimi, "Technology Development and Future Prospects for Large-Scale Hydrogen Storage & Transportation (1);" Bulletin of the High Pressure Gas Safety Institute of Tokyo, August and Sep. 2019; 10 pp.
Basic Hydrogen Stragegy, Ministerial Council on Renewable Energy, Hydrogen and Related Issues, Dec. 26, 2017; 37 pp.
Notification of Second Office Action for Chinese Patent Application No. 202080099971.X dated Nov. 1, 2024; 27 pp.

* cited by examiner

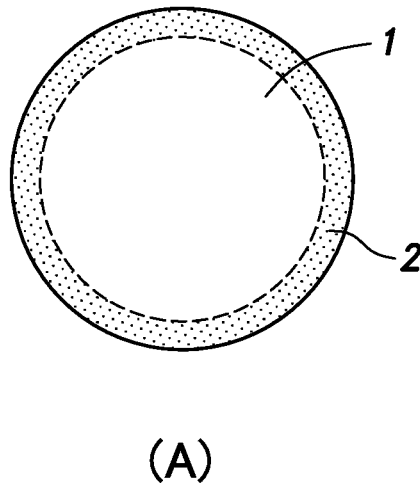
(A)
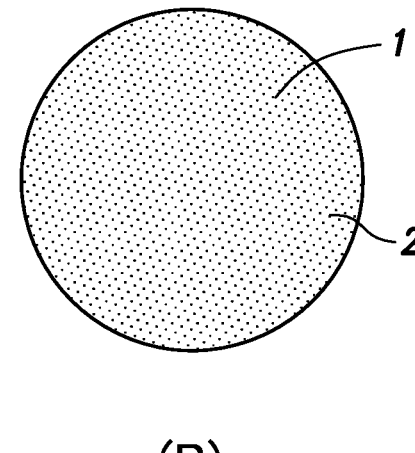
(B)

UNIFORM-TYPE PLATINUM-LOADED ALUMINA CATALYST, METHOD OF PRODUCING SAME, AND METHOD OF USING SAME

CROSS-REFERENCE TO RELATED APPLICATION

This application is a U.S. National Phase Application of International Patent Application No. PCT/JP2020/017563, filed Apr. 23, 2020, the contents of which are hereby expressly incorporated by reference in their entirety.

TECHNICAL FIELD

The present invention relates to a metal catalyst for use in processes using catalyst, such as chemical product production, hydrogen production, fine chemical production, environment cleaning such as exhaust gas treatment, etc., and relates to a uniform-type platinum-loaded alumina catalyst in which platinum is loaded on an alumina carrier, a method of producing the same, and a method of using the same.

BACKGROUND ART

A platinum-loaded alumina catalyst in which platinum or the like is loaded on an alumina carrier is industrially used in a very wide range of fields, such as production of fuel, petrochemical products, and fine chemicals such as medicine or environmental clean-up such as cleaning automobile exhaust gas, through dehydrogenation reaction, hydrogenation reaction, and reforming reaction of various compounds, such as dehydrogenation reaction of dehydrogenating hydrogenated aromatics such as methylcyclohexane, cyclohexane, decalin, and dibenzyltoluene, for example, into the corresponding aromatics and hydrogen.

Generally, such platinum-loaded alumina catalyst is manufactured as follows: a porous alumina carrier made of a metal oxide of alumina is prepared; the obtained porous alumina carrier is impregnated with a solution of a catalyst metal compound, such as a chloroplatinic acid aqueous solution, a platinum ammonium chloride aqueous solution, and a solution of an organoplatinum compound such as platinum acetylacetonate; the resultant is dried to form a dried matter on which the catalyst metal compound is loaded; the dried matter is calcined, e.g., at 350 to 800° C. for 0.5 to 24 hours to form a calcined matter on which the catalyst metal compound is loaded; and, as required, the obtained calcined matter on which the catalyst metal compound is loaded is subjected to hydrogen reduction, e.g., at 250 to 800° C. for 0.5 to 24 hours.

Regarding the platinum-loaded alumina catalyst manufactured by such a method, it is known that since the platinum atom with the atomic weight 195 has a large mass and the adsorbability of a platinum compound used as a platinum source to the catalyst carrier is high, the platinum compound is adsorbed by and fixed to the outer shell part of the alumina carrier before the platinum compound is dispersed to the inside of the alumina carrier, which forms a so-called egg shell-type platinum-loaded catalyst in which, when the dispersion state of platinum metal is observed in the catalyst cross section, the platinum metal is loaded only on the outer shell part of the catalyst and no platinum metal is loaded inside the carrier.

In the catalytic reaction in which the diffusion resistance inside the catalyst particles is high due to reasons such as that raw material molecules are large, the reaction occurs preferentially in the outer shell of the catalyst particles even if platinum as the active metal is loaded to the inside of the catalyst because the speed of diffusion of the raw material molecules to the inside of the catalyst is slow and the reaction does not progress sufficiently. In such a reaction, the egg shell-type catalyst in which the active metal exists in only the outer shell part of the catalyst is advantageous. However, when a certain amount of active metal is loaded only on the outer shell of the catalyst particles, the density of the active metal particles increases, which may lead to problems that the active metal particles cannot be sufficiently dispersed, catalyst deterioration due to sintering or coking is likely to occur, etc. From such a viewpoint, catalysts in which the dispersity of platinum metal when platinum metal is loaded only on the outer shell part of the catalyst is improved are being developed. Patent Document 1 discloses an egg shell-type platinum-loaded alumina catalyst in which the pore size of the platinum-loaded alumina catalyst is substantially uniform to such a degree that the diffusion resistance does not become large and the dispersion of platinum is good. Also, catalysts in which platinum metal is dispersed well over the entire cross section of the catalyst so that the surface area of the carrier is fully utilized in a reaction not affected by the diffusion resistance are being developed, and Patent Document 2 discloses such a uniform-type platinum-loaded alumina catalyst.

The platinum-loaded alumina catalyst has been used in the catalytic process of a wide range of fields from old times, but in recent years is used in an organic chemical hydride method which is one method for hydrogen energy carrier and is attracting attention as storage and transportation technology for hydrogen energy. Development of platinum-loaded alumina catalyst having higher performance compared to the conventional platinum-loaded alumina catalyst is being in progress, and Patent Document 1 and Patent Document 2 disclose, as a use of the platinum-loaded alumina catalyst, use in the dehydrogenation reaction necessary in the organic chemical hydride method. The organic chemical hydride method is a method for "storing" and "transporting" hydrogen in the form of organic chemical hydride compounds (hydrogenated organic compounds) in which hydrogen is taken in the molecular structure of chemical products by chemical reaction. The organic chemical hydride method is a method that has been proposed since 1980s. However, the life of dehydrogenation catalyst for producing hydrogen from the organic chemical hydride compounds in which hydrogen is retained is very short, whereby industrial implementation thereof is difficult and the method has not been put into practice. The key to technological development is development of a novel dehydrogenation catalyst having sufficient performance such as a catalyst life that allows for industrial use. Currently, due to application of a platinum-loaded alumina catalyst having high performance as mentioned above, the development of a hydrogen energy carrier system based on the organic chemical hydride method has reached a point where demonstration of large-scale international hydrogen transportation is executed, and the development has technologically progressed to a stage where commercialization is possible. Non-Patent Documents 3 and 4 disclose details of such development of the organic chemical hydride method.

Japan has adopted a policy to promote practical implementation and dissemination of hydrogen energy as a national policy from the Fourth Strategic Energy Plan after the Great East Japan Earthquake, and following formulation of the Hydrogen Fuel Cell Technology Roadmap, the Hydrogen Basic Strategy was approved by the cabinet in 2017. The aforementioned organic chemical hydride method can provide a hydrogen energy carrier for "storing" and "transporting" hydrogen energy in a large scale, and the practical implementation thereof is incorporated in the Hydrogen Basic Strategy, which sets 30 ¥/Nm$^3$ as a target hydrogen supply price by 2030, and 20 ¥/Nm$^3$ by 2050. This requires cost reduction by continuous improvement technology development, and improvement of the catalyst performance, particularly the catalyst life, significantly affects the cost reduction. The development has progressed such that of the catalyst performance, the conversion rate, the selectivity, and the yield, which is a product of the conversion rate and the selectivity, have been improved to a relatively high level, and the development is now in a stage where improvement of the catalyst life, which determines how long the performance can be maintained, contributes to the cost reduction.

PRIOR ART DOCUMENT(S)

Patent Document(s)

Patent Document 1: JP4652695B2
Patent Document 2: JP4142733B2
Non-Patent Document 3: OKADA Yoshimi, Energy/Natural Resources, Vol. 33, No. 3, 168 (2018)
Non-Patent Document 4: OKADA Yoshimi, Bulletin of The High Pressure Gas Safety Institute of TOKYO, August and September 2019
Non-Patent Document 5: Agency for Natural Resources and Energy, Hydrogen Basic Strategy (December 2017)

SUMMARY OF THE INVENTION

Task to be Accomplished by the Invention

The uniform-type platinum-loaded alumina catalyst of Patent Document 2 has a relatively long catalyst life and is practically useful, but further improvement is desired. Since the dehydrogenation reaction in the organic chemical hydride method is an endothermic reaction and an equilibrium reaction in which the number of molecules increases with the reaction, the efficiency is better under the reaction conditions at higher temperature and lower pressure. On the other hand, since the produced hydrogen may be preferred to be at high pressure depending on usage, a catalyst that can be used at higher reaction temperature may be demanded. However, under the reaction conditions at high temperature, side reaction tends to occur, and therefore, it is necessary to improve the selectivity of the catalyst. Also, under the reaction conditions at high temperature, carbon tends to be produced on the catalyst and the catalyst tends to deteriorate easily. Therefore, a catalyst for dehydrogenation reaction which achieves high selectivity, reduced production of carbon, and long life under the reaction conditions at high temperature is desired.

Under the above background, the present inventors carried out extensive research on the performance improvement of the uniform-type platinum-loaded alumina catalyst and, as a result, found that in relation to the uniform-type platinum-loaded alumina catalyst in which sulfur is dispersed substantially uniformly over the entire cross section of the alumina carrier and platinum metal particles likewise are dispersed substantially uniformly over the entire cross section of the alumina carrier, addition of alkali metal can improve the catalyst life.

Accordingly, an object of the present invention is, in relation to a uniform-type platinum-loaded alumina catalyst using sulfur, to provide a platinum-loaded alumina catalyst demonstrating excellent performance in terms of catalytic activity, selectivity, and catalyst life.

Also, another object of the present invention is to provide such a uniform-type platinum-loaded alumina catalyst demonstrating excellent performance in terms of catalytic activity, selectivity, and particularly catalyst life, a method of producing the same, and a method of using the same.

Means to Accomplish the Task

One aspect of the present invention is a uniform-type platinum-loaded alumina catalyst, comprising: an alumina carrier; sulfur or a sulfur compound dispersed over an entire cross section of the alumina carrier; platinum dispersed and loaded over the entire cross section of the alumina carrier; and one or more alkali metals selected from the group consisting of sodium, potassium, and calcium. According to this aspect, the catalyst life can be improved than in the uniform-type platinum-loaded alumina catalyst disclosed in Patent Document 2.

Preferably, a content of the platinum is 0.05 to 5.0 wt % calculated as elemental platinum. Also preferably, a content of the sulfur or the sulfur compound is 0.15 to 5.0 wt % calculated as elemental sulfur. A content of the alkali metal(s) preferably is 0.1 to 5.0 wt % calculated as elemental alkali metal.

Another aspect of the present invention is a method of producing a uniform-type platinum-loaded alumina catalyst, comprising: a step of preparing a uniform-type platinum-loaded alumina catalyst; a step of impregnating the uniform-type platinum-loaded alumina catalyst with an aqueous solution of alkali metal compound and thereafter drying the impregnated catalyst; and a step of reducing the dried uniform-type platinum-loaded alumina catalyst in a hydrogen atmosphere or calcining the dried uniform-type platinum-loaded alumina catalyst and thereafter reducing the calcined catalyst in a hydrogen atmosphere.

Yet another aspect of the present invention provides a method of dehydrogenating a hydrogenated aromatic, comprising dehydrogenating a hydrogenated aromatic by using the uniform-type platinum-loaded alumina catalyst. Preferably, the hydrogenated aromatic is one member or a mixture of two or more members selected from the group consisting of a hydride of monocyclic aromatic, a hydride of bicyclic aromatic, and a hydride of compound having 3 or more aromatic rings. Also preferably, the hydrogenated aromatic is one member or a mixture of two or more members selected from the group consisting of methylcyclohexane, cyclohexane, dimethylcyclohexane, tetralin, decalin, methyldecalin, biphenyl, diphenylmethyl, dibenzotriol, and tetradecahydroanthracene.

As described above, the uniform-type catalyst is effective when the raw material is sufficiently diffused to the inside of the catalyst, and the egg shell-type catalyst is effective when the diffusion to the inside of the catalyst is limited and is not performed sufficiently, and therefore, it is preferred to use these two types of catalysts properly depending on the state of diffusion in the reaction field. Also, even with the same reaction, the state of diffusion of the raw material to the inside of the catalyst may differ depending on the position in the reactor, and near the exit where the reaction has progressed, the raw material concentration becomes low, and the diffusion to the inside of the catalyst may be limited. In such a case, it is preferred to use both of the uniform-type and egg shell-type catalysts in the reactor.

In general, the extent of diffusion of the raw material to the inside of the catalyst is represented by a catalyst effectiveness factor, and the catalyst effectiveness factor can be controlled by changing the size and shape of the catalyst pellet. Thus, for both of the uniform-type and egg shell-type catalysts, it is possible to produce platinum-alumina catalysts having various catalyst effectiveness factors by changing the size and shape of the catalyst pellet.

In the uniform-type platinum-loaded alumina catalyst of the present invention, it is preferred that the alumina carrier on which sulfur or a sulfur compound exists has pore sizes controlled as uniformly as possible. Specifically, a porous metal oxide in which a sulfur-containing porous metal oxide has a surface area of 150 $m^2/g$ or more, a pore volume of 0.4 $cm^3/g$ or more, and an average pore diameter of 40 to 300 Å, with pores having a pore diameter in a range of ±30 Å from the average pore diameter occupying 60% or more of a total pore volume is preferred. As a result of that the pore sizes are made uniform as this, the alumina carrier has a uniform pore size over the entirety of the powder and molded body thereof. As a result, it becomes advantageous in a process of dispersing and loading sulfur on the alumina carrier and a process of dispersing and loading metal over the entirety in correspondence with the distribution of sulfur.

Patent Document 1 discloses a platinum-loaded alumina catalyst in which platinum is loaded on a porous γ-alumina carrier having a surface area of 150 $m^2/g$ or more, a pore volume of 0.55 $cm^3/g$ or more, and an average pore diameter of 90 to 300 Å, with pores having a pore diameter of 90 to 300 Å occupying 60% or more of a total pore volume. This catalyst is a general egg shell-type platinum-loaded alumina catalyst as described above, and Patent Document 1 also discloses a catalyst to which alkali metal is added as means to improve the catalyst life. When using a catalyst with alumina as a carrier, merely inhibiting the decomposition reaction that occurs on the platinum particles is not enough, and it is also necessary to inhibit the decomposition reaction that occurs on the acid sites of the alumina. Therefore, in many cases, the decomposition reaction occurring on the alumina surface is inhibited by masking these acid sites using alkali metals such as potassium and lithium. From this viewpoint, Patent Document 1 discloses that in the egg shell-type platinum-loaded catalyst, loading of platinum with high dispersity inhibits the decomposition on platinum, and addition of alkali to mask the acid sites on alumina has a remarkable effect on the catalyst life improvement.

On the other hand, Patent Document 2 discloses a uniform-type platinum-loaded alumina catalyst in which sulfur is contained in the alumina carrier so that the dispersion mode of the loaded platinum becomes a uniform-type and the decomposition reaction is suppressed to improve the catalyst life. At the time when the invention of Patent Document 2 was made, it was considered that in the case where the alumina carrier containing sulfur or a sulfur compound is used, even when the acid sites are not masked with alkali metal thereon, the decomposition reaction inhibitory effect is equivalent to or higher than the inhibitory effect when the acid sites are masked with alkali metal. Although the detailed mechanism is not elucidated, it was considered that elemental sulfur forms a complex oxide with alumina, thereby altering the configuration of the acid sites, which remain in the case of using alumina alone, to a different configuration. In that case, the form obtained when elemental sulfur forms a complex oxide with alumina is generally considered to be in a sulfate group form. The sulfate group itself is acidic and the number of acid sites, i.e., acidity, presumably increases by the existence thereof. However, it is estimated that these acid sites do not contribute to progress of the decomposition reaction at a relatively low reaction temperature, and therefore, it was considered that in the uniform-type platinum-loaded alumina catalyst that uses sulfur, the addition of alkali metal was unnecessary.

However, as a result of extensive research on whether the addition of alkali metal has effect or not, it was found by the reaction test that, contrary to the initial expectation, the activity deterioration was inhibited more and the catalyst life became longer in the uniform-type platinum-loaded alumina catalyst than in the conventional uniform-type platinum-loaded alumina catalyst that uses sulfur. In the catalyst production, additional inclusion of the alkali addition process can be a cause of cost increase, but the cost reduction effect brought by the extension of the catalyst life according to the present invention is much greater than the increase in the catalyst production cost, and it is possible to extend the replacement life of the reactor the dehydrogenation catalyst from the conventional 1 to 2 years to 3 to 4 years depending on how the catalyst is used.

The present catalyst is typically used as a dehydrogenation catalyst, in which the catalyst fills the catalytic reaction tubes of a heat exchange-type reactor. As with general heat exchanges, the number of the catalytic reaction tubes may be thousands in a large reactor. When the platinum-loaded alumina catalyst used in such a reactor reaches a catalyst life, at which time the performance is lowered to result in a certain yield, the catalyst is removed to be replaced with new catalyst. Platinum is recovered from the removed waste catalyst and is recycled for use in the production of the catalyst for next replacement. The removing work may take several days, and the charging of the new catalyst may require more working days, and therefore, the catalyst replacement requires about two weeks. The production stops during that time, and therefore, the reduction of replacement frequency significantly contributes to the cost reduction. Namely, while the life of the catalysts disclosed by Patent Document 1 and Patent Document 2 is 1 to 2 years, the life of the alkali-added uniform-type platinum-loaded alumina catalyst according to the present invention is 4 years, and this makes it possible to reduce the catalyst replacement frequency to half or less.

Effect of the Invention

The uniform-type platinum-loaded alumina catalyst of the present invention has higher catalyst performance, particularly with respect to the catalyst life, compared to the conventional uniform-type platinum-loaded alumina catalyst. Also, these catalysts can be mass-produced easily by existing catalyst production facilities according to the manufacturing method of the present invention. These catalysts not only can be used as an alternative to the existing platinum-loaded alumina catalyst, but also can be favorably used as a dehydrogenation catalyst for methylcyclohexane or the like in the organic chemical hydride method, which is one of the hydrogen storage and transportation technologies.

BRIEF DESCRIPTION OF THE DRAWINGS

FIG. 1 is an explanatory diagram showing (A) an egg shell-type metal-loaded catalyst and (B) a uniform-type metal-loaded catalyst.

MODE(S) FOR CARRYING OUT THE INVENTION

First, an egg shell-type metal-loaded catalyst and a uniform-type metal-loaded catalyst of the present invention will be described with reference to FIG. 1. The egg shell-type metal-loaded catalyst refers to a state where a metal member to be loaded is dispersed and loaded only on the outer shell part of the cross section of a molded catalyst. Namely, a metal loading part 2 on which the metal member is loaded is formed in the outer shell part of a porous carrier 1. The uniform-type metal-loaded catalyst refers to a state where a metal member is dispersed over the entire cross section of the catalyst and the metal loading part 2 on which the metal member is loaded is formed over the entire inside of a molded body of the porous carrier 1.

The uniform-type platinum-loaded alumina catalyst includes an alumina carrier, sulfur or a sulfur compound dispersed over the entire cross section of the alumina carrier, platinum dispersed and loaded over the entire cross section of the alumina carrier, and one or more alkali metals selected from the group consisting of sodium, potassium, and calcium.

Next, the alumina carrier used in the present invention will be described. The alumina carrier has a surface area of $150 \, \text{m}^2/\text{g}$ or more, a pore volume of $0.40 \, \text{cm}^3/\text{g}$ or more, and an average pore diameter of 40 to 300 Å, with pores having a pore diameter in a range of ±30 Å from the average pore diameter occupying 60% or more of a total pore volume.

The alumina carrier preferably is a porous γ-alumina carrier. As disclosed in JPH6-72005B2, for example, the alumina carrier preferably is a porous γ-alumina carrier obtained by washing by filtration a slurry of aluminum hydroxide generated by neutralizing aluminum salt, dehydrating and drying the obtained alumina hydrogel, and then calcining the resultant at 400 to 800° C. for about 1 to 6 hours. More preferably, the alumina carrier is a porous γ-alumina carrier obtained through a pH swing process in which the pH of alumina hydrogel is alternately fluctuated between a pH range of the dissolution of alumina hydrogel and a pH range of the precipitation of boehmite gel and simultaneously an alumina hydrogel forming substance is added for growing crystals of the alumina hydrogel when the pH is fluctuated from at least either one of the pH ranges to the other one of the pH ranges. The porous γ-alumina carrier obtained through the pH swing process is excellent in the uniformity of pore distribution, and excellent in that the physical properties of each pellet are stable because there is less variation in the physical properties also in the alumina carrier pellet after the formation of the carrier.

There is no limitation on the sulfur or sulfur compound to be dispersed in the alumina carrier beforehand for incorporation thereof insofar as the sulfur or sulfur compound has a sulfur element and can be uniformly dispersed in the catalyst carrier during the preparation of the catalyst carrier or after the preparation of the catalyst carrier. For example, sulfur crystal powders, and sulfur-containing compounds such as sulfuric acid, sulfate including ammonium sulfate can be mentioned. From the viewpoint that sulfur is likely to disperse on a carrier, sulfur compounds having solubility in water or an organic solvent are preferable, and sulfuric acid, ammonium sulfate, etc., can be mentioned as such sulfur compounds.

The amount of sulfur to be contained in a carrier is preferably 0.15 to 5.0 wt %, and more preferably 0.15 to 3.0 wt %, calculated as elemental sulfur. When the sulfur content is less than 0.15 wt %, the degree that metal is uniformly loaded as far as the center of the catalyst is low, while when the sulfur content exceeds 5 wt %, a problem is likely to occur that sulfur is likely to locally agglomerate and metal is not dispersed and loaded on such a portion. In view of the above, the most suitable sulfur content range is 0.15 to 5.0 wt % considering the effect that metal is uniformly dispersed and loaded.

In the present invention, with respect to a method of preparing a sulfur-containing catalyst carrier containing the above-mentioned sulfur or sulfur compound, usable is a method capable of incorporating the sulfur or sulfur compound in a state where the sulfur or sulfur compound is uniformly dispersed throughout the cross section of the carrier. For example, the following methods are mentioned: method A involving kneading sulfur powder in a metal hydroxide gel serving as a precursor of a metal oxide obtained when preparing a catalyst carrier, forming the resultant into a predetermined shape, and drying and calcining the resultant; method B involving preparing a metal hydroxide gel serving as a precursor of a metal oxide containing sulfur using metal sulfate and/or sulfuric acid when preparing a catalyst carrier, forming the resultant into a predetermined shape, and drying and calcining the resultant; method C involving forming a metal hydroxide gel serving as a precursor of a metal oxide into a predetermined shape when preparing a catalyst carrier, drying the resultant to form a dry metal hydroxide gel, impregnating the dry metal oxide with a sulfur compound solution, and calcining the same; method D involving forming a metal hydroxide gel serving as a precursor of a metal oxide into a predetermined shape when preparing a catalyst carrier, drying the resultant to form a dry metal hydroxide, impregnating the dry metal hydroxide with a sulfur compound solution, and calcining the same; and method E involving forming a metal hydroxide gel serving as a precursor of a metal oxide into a predetermined shape, drying the resultant to form a dry metal hydroxide gel, calcining the dry metal hydroxide gel to form a calcined metal oxide, impregnating the calcined metal oxide with a sulfur compound solution such as an sulfuric acid aqueous solution and an ammonium sulfate solution, and further calcining the resultant.

With respect to calcining conditions when preparing the sulfur-containing catalyst carrier, usually, the calcining temperature is 100 to 1000° C., and preferably 350 to 800° C., and the calcining time is 0.5 to 48 hours, and preferably 1 to 24 hours. When the calcining temperature is lower than 350° C., conversion to an oxide from a hydroxide may not be fully performed, while when the calcining temperature is higher than 800° C., the surface area after calcining may be dramatically reduced.

In the present invention, the amount of platinum to be loaded on the aforementioned sulfur-containing catalyst carrier is 0.05 to 5.0 wt %, preferably 0.1 to 3.0 wt %, calculated as elemental platinum. When the loading amount of platinum is less than 0.05 wt %, there is a problem that the activity is low, while when the loading amount of platinum exceeds 5.0 wt %, there are problems that the particle diameter of platinum increases, the selectivity is reduced, sintering is likely to occur, resulting in that deactivation is likely to occur.

In the present invention, when platinum metal is loaded on the alumina carrier, the above-mentioned alumina carrier may be impregnated with a solution of platinum compound, dried, and then calcined at a predetermined temperature. As the platinum compound, chloride, bromide, ammonium salt, carbonyl compound, or various complex compounds, such as an amine complex, an ammine complex, and an acetylacetonato complex, of platinum can be mentioned. The platinum compound may be, for example, chloroplatinic acid, platinum acetylacetonate, ammonium platinate, bromo platinate, platinum dichloride, platinum tetrachloride hydrate, platinum carbonyl dichloride, or the like.

After the alumina carrier is impregnated with the above-mentioned solution of platinum compound, the alumina carrier to which the platinum compound adheres is dried at 50 to 200° C. for 0.5 to 48 hours, and thereafter is calcined at 350 to 600° C. for 0.5 to 48 hours, more preferably at 350 to 450° C. for 0.5 to 5 hours.

The amount of alkali that is added to the uniform-type platinum-loaded alumina catalyst is 0.1 to 5.0 wt %, preferably 0.3 to 3.0 wt %, and more preferably 0.5 to 1.5 wt %. When the loading amount of alkali metal is less than 0.1 wt %, there is a problem that the catalyst life is short and the effect is low, while when the loading amount is more than 5.0 wt %, there is a problem that the activity is lowered and the catalyst life is shortened.

The compound of the alkaline metal used when loading the alkaline metal to the uniform-type platinum-loaded alumina catalyst may be, for example, a chloride, bromide, iodide, nitrate, sulfate, acetate, propionic acid, and the like of the alkaline metal, which preferably is water soluble and/or soluble to an organic solvent such as acetone. Such a compound may be, for example, sodium chloride, sodium bromide, sodium iodide, sodium nitrate, sodium sulfate, sodium acetate, sodium propionate, potassium chloride, potassium bromide, potassium iodide, potassium nitrate, potassium sulfate, potassium acetate, potassium propionate, calcium chloride, calcium bromide, calcium iodide, calcium nitrate, calcium sulfate, calcium acetate, calcium propionate, or the like.

When the alkaline metal is loaded on the uniform-type platinum-loaded alumina catalyst, the uniform-type platinum-loaded alumina catalyst is impregnated with a solution of a compound of the alkaline metal, thereafter dried under a drying condition at room temperature to 200° C. for 0.5 to 48 hours, preferably at 50 to 150° C. for 0.5 to 24 hours, more preferably at 80 to 120° C. for 0.5 to 5 hours, and then calcined at 350 to 600° C. for 0.5 to 48 hours, preferably at 350 to 450° C. for 0.5 to 5 hours.

The dried matter on which the alkali metal is loaded, which is obtained by impregnating the uniform-type platinum-loaded alumina catalyst with the alkali metal and drying the impregnated catalyst, is eventually subjected to hydrogen reduction and is used in a reaction. The reduction condition of this hydrogen reduction is preferably at 350 to 600° C. for 0.5 to 48 hours, more preferably at 350 to 550° C. for 3 to 24 hours in a hydrogen gas atmosphere. If the temperature at the time of the hydrogen reduction is lower than 350° C., there arises a problem that platinum is not fully reduced, and if the temperature at the time of the hydrogen reduction exceeds 600° C., there arises a problem that sintering of platinum particles occurs at the time of reduction, and the metal dispersion degree is lowered.

The method of producing the uniform-type platinum-loaded alumina catalyst includes a step of preparing a uniform-type platinum-loaded alumina catalyst, a step of impregnating the uniform-type platinum-loaded alumina catalyst with an aqueous solution of alkali metal compound and thereafter drying the impregnated catalyst, and a step of reducing the dried uniform-type platinum-loaded alumina catalyst in a hydrogen atmosphere or calcining the dried uniform-type platinum-loaded alumina catalyst and thereafter reducing the calcined catalyst in a hydrogen atmosphere.

The uniform-type platinum-loaded alumina catalyst of the present invention is used, for example, as a dehydrogenation catalyst for a hydrogenated aromatic, which is utilized as a hydrogen energy carrier in the organic chemical hydride method, which is one of the methods for storing and transporting the hydrogen energy. The hydrogenated aromatic preferably is one member or a mixture of two or more members selected from the group consisting of a hydride of monocyclic aromatic, a hydride of bicyclic aromatic, and a hydride of compound having 3 or more aromatic rings. Also, the hydrogenated aromatic preferably is one member or a mixture of two or more members selected from the group consisting of methylcyclohexane, cyclohexane, dimethylcyclohexane, tetralin, decalin, methyldecalin, biphenyl, diphenylmethyl, dibenzotriol, and tetradecahydroanthracene.

When the platinum-loaded alumina catalyst is used in the dehydrogenation reaction of a hydrogenated aromatic such as methylcyclohexane in the organic chemical hydride method, catalyst deterioration is observed, in which the performance decreases gradually as the reaction time passes. The cause of the catalyst deterioration is carbon precipitation called coking. Coking is a phenomenon in which carbon precipitation occurs on the surface of platinum metal, which is an active metal mainly due to decomposition reaction of the raw material compound such as methylcyclohexane, and as a result, the effective active sites of the active metal are covered and do not function.

The catalytic reaction deterioration phenomenon is observed as a decrease of the conversion rate in the reaction test, and in the case of dehydrogenation reaction of a hydrogenated aromatic, it is known that the phenomenon is observed as a linear decrease of the conversion rate. Accordingly, by observing the change of the conversion rate over time in the reaction test, it is possible to evaluate relative superiority or inferiority of the catalyst life based on the inclination of the decrease. Further, since the conversion rate decreases linearly not only under actual reaction conditions but also in an accelerated reaction test for evaluating the catalyst life in a short time, it is possible to evaluate the catalyst life.

Hydrogen attracted attention as clean secondary energy from 1970s, and in Japan, research and development of hydrogen production technologies and fuel cells were promoted in the Sunshine Project from 1974 to 1992, the Moonlight Project from 1978 to 1992, and the New Sunshine Project from 1993 to 2001. Regarding large-scale storage and transportation technology of hydrogen, development of liquefied hydrogen method was started in the WE-NET project from 1992 to 2002. On the other hand, the history of development of the organic chemical hydride method is old, and goes back to the Euro-Quebec project which was carried out in 1980s as an international research and development project by Canada's Quebec government and twelve European countries. This plan proposed producing hydrogen by performing water electrolysis by using excess hydroelectric power abundantly present in Quebec and transporting the hydrogen across the Atlantic Ocean for use in Europe. As a hydrogen transportation method, discussion was made on the liquid hydrogen method as a first candidate, the liquid ammonia method as a second candidate, and the organic chemical hydride method as a third candidate. At that time, the organic chemical hydride method was called an MCH method. The Euro-Quebec project continued till about 1992 for approximately 10 years but the project ended with none of the methods being practically implemented, and since then, technology for large-scale hydrogen store and transport has not been practically implemented.

In Japan, development of the liquefied hydrogen method was promoted in WE-NET project implemented from 1992 to 2002, while the research of the organic chemical hydride method was promoted mainly by Japanese universities. The applicant started the development of dehydrogenation catalyst in 2002 and made a first academic presentation in the World Hydrogen Energy Conference held in Yokohama in 2004, and from around this time, examples of research and development at companies were started to be released. At the present time, the large-scale hydrogen storage and transportation technologies for which research and development have been advanced to a demonstration level are only the liquefied hydrogen method and the organic chemical hydride method, which is proposed by the applicant.

The organic chemical hydride method (OCH method) is a method in which hydrogen is subjected to hydrogenation reaction with an aromatic such as toluene (TOL) and converted to a saturated cyclic compound such as methylcyclohexane (MCH) having the hydrogen taken in the molecule thereof so that "storage" and "transportation" are achieved in a liquid state under normal temperature and normal pressure and a necessary amount of hydrogen is taken out by dehydrogenation reaction and used at the place of use. Thus, the method includes a hydrogenation reaction (hydrogen storage reaction) for making hydrogen react with toluene and a dehydrogenation reaction (hydrogen generation reaction) for generating hydrogen from MCH and recovering toluene. TOL generated after taking out hydrogen is recovered and repeatedly used as a container (carrier) of hydrogen.

Since hydrogen is an explosive gas, there is a potentially high risk in storing and transporting hydrogen as it is in a large scale. In the present method, storage and transportation of hydrogen is performed with the hydrogen being retained in the molecule of MCH, which is a component of gasoline and diesel oil and is in the liquid state under normal temperature and normal pressure, and therefore, this method is highly safe in principle. Specifically, even if the tank and the reactor of the present system are caught in a fire, it would be similar to conventional oil refinery fires, and it is considered that the possibility of causing severe damage to the surrounding urban area is very low. The thought "accidents will eventually happen" is very important to safety measures, and that is why it is required to be safe in principle.

With this method, it is possible to store about 530 L of hydrogen gas in 1 L of liquid MCH. To physically decrease the volume of hydrogen gas to $\frac{1}{500}$ or less, it is necessary to compress the hydrogen gas to 500 atm or higher or to cool the hydrogen gas to $-253°$ C. or lower to make it liquid hydrogen which is $\frac{1}{800}$ in volume, but according to the present method, by use of chemical reaction it is possible to decrease the volume to $\frac{1}{500}$ under normal temperature and normal pressure. Also, since TOL and MCH are in the liquid state in a wide temperature range of $-95$ to $101°$ C., they can be handled as a liquid such as water under any environment on the Earth. To establish a large-scale supply chain, it is necessary to procure hundreds of thousands of tons of TOL, but TOL is a fuel base material contained in high octane gasoline in a proportion of 10 wt % or more and also is a general purpose chemical product produced in 20 million tons per year worldwide to be used widely as industrial solvent. Therefore, TOL can be easily procured in large amounts.

From the foregoing, the primary feature of the present method is high safety that can lower the potential risk regarding large-scale storage and transportation of hydrogen to the level of the risk related to conventional gasoline storage and transportation in principle, and this is the first reason why the applicant focused on this method. Also, storage of TOL and MCH in large tanks and transportation of the same by chemical tankers and chemical lorries have been practically implemented from old times as chemical products. In the current trend of electrification of automobiles, demand for gasoline and diesel oil as automobile fuels is expected to decrease and the existing infrastructure therefor, such as storage tanks, could be diverted. This can be a significant merit.

Further, in a case where hydrogen is used in large scale as fuel for power generation in the future, it is expected that hydrogen fuel reserve will become necessary as the current oil reserve. TOL and MCH do not chemically change even if stored for a long period and in large scale, and there is no extra energy consumption or loss due to long-term storage, and therefore, by storing MCH in the tanks of current oil reserve base, it is possible to convert the oil reserve bae to a reserve base for hydrogen energy.

The applicant focused on the organic chemical hydride method which has the highest safety and is advantageous in cost because the existing infrastructure can be diverted, started the development of novel dehydrogenation catalyst, which is the key to practical implementation, in 2002, and succeeded first in the world in developing novel dehydrogenation catalyst that can be industrially applicable to the organic chemical hydride method. Thereafter, for the purpose of establishment of technology for the whole system, the applicant used the developed catalyst in the dehydrogenation process and combined it with the toluene hydrogenation process, which realizes hydrogen storage reaction, to construct a demonstration plant which continuously repeats the hydrogen storage and hydrogen generation at the same place in 2013. The demonstration operation was conducted from April 2013 to November 2014 for about 10,000 hours in total, and it was confirmed that high performance as designed could be maintained stably, whereby the establishment of the technology was completed.

Thereafter, as the final stage of the development, a first-in-the-world demonstration of international hydrogen supply chain, in which about 200 tons of hydrogen will be actually transported from Brunei in Southeast Asia to Kawasaki waterfront in Japan by use of the present system, will be carried out as a project of NEDO (New Energy and Industrial Technology Development Organization) in 2020.

Japan has adopted a policy to promote practical implementation and dissemination of hydrogen energy as a national policy from the Fourth Strategic Energy Plan after the Great East Japan Earthquake, and following formulation of the Hydrogen Fuel Cell Technology Roadmap, the Hydrogen Basic Strategy was approved by the cabinet in 2017. Practical implementation of the aforementioned organic chemical hydride method is incorporated, as a hydrogen energy carrier for "storing" and "transporting" hydrogen energy in a large scale, in the Hydrogen Basic Strategy, which sets 30 ¥/Nm$^3$ as a target hydrogen supply price by 2030, and 20 ¥/Nm$^3$ by 2050. This requires cost reduction by continuous improvement technology development, and improvement of the catalyst performance is an important element of the cost reduction. Thus, the present invention is effective in the practical implementation of the organic chemical hydride method and highly useful industrially.

The uniform-type platinum-loaded alumina catalyst not only can be used as a catalyst but also can be effectively used as an adsorbent or the like. The uniform-type platinum-loaded alumina catalyst is also useful as a filler of guard columns for preprocessing of adsorbing impurities and the like in the catalytic reaction process to which the catalyst of the present invention can be applied, as application to the organic chemical hydride method.

The uniform-type platinum-loaded alumina catalyst according to the present embodiment may be used together with an egg shell-type platinum-loaded alumina catalyst. The egg shell-type second component-added platinum-loaded alumina catalyst preferably includes an alumina carrier, platinum dispersed and loaded on an outer shell of the alumina carrier, and one or more second components selected from the group consisting of vanadium, chrome, molybdenum, and phosphorous. The alumina carrier preferably has a surface area of 150 m²/g or more, a pore volume of 0.40 cm³/g or more, and an average pore diameter of 40 to 300 Å, with pores having a pore diameter in a range of ±30 Å from the average pore diameter occupying 60% or more of a total pore volume. The amount of platinum loaded on the alumina carrier is 0.05 to 5.0 wt %, preferably 0.1 to 3.0 wt %. The egg shell-type platinum-loaded alumina catalyst may contain the second component for the purpose of life extension. The amount of addition of the second component is 0.1 to 5 wt %, preferably 0.3 to 3.0 wt %, and more preferably 0.5 to 2.0 wt %. The compound of the second component used when adding the second component to the egg shell-type platinum-loaded alumina catalyst may be, for example, a chloride, bromide, iodide, nitrate, sulfate, acetate, propionic acid, and the like of the second component element, which preferably is water soluble and/or soluble to an organic solvent such as acetone. Such a compound may be, for example, vanadium chloride, vanadium bromide, vanadium iodide, vanadium nitrate, vanadium sulfate, vanadium acetate, vanadium propionate, chromium chloride, chromium bromide, chromium iodide, chromium nitrate, chromium sulfate, chromium acetate, chromium propionate, molybdenum chloride, molybdenum bromide, molybdenum iodide, molybdenum nitrate, molybdenum sulfate, molybdenum acetate, molybdenum propionate, phosphoric acid, inorganic phosphate such as ammonium dihydrogen phosphate, organophosphate compound, or the like.

The egg shell-type second component-added platinum-loaded alumina catalyst and the uniform-type platinum-loaded alumina catalyst may be charged in the same reactor. The egg shell-type second component-added platinum-loaded alumina catalyst and the uniform-type platinum-loaded alumina catalyst may be arranged in series or may be arranged in a mutually mixed manner.

In this way, the uniform-type platinum-loaded alumina catalyst can be favorably used in the dehydrogenation reaction of hydrogenated aromatic, such as methylcyclohexane, used as a hydrogen energy carrier, and contributes to practical implementation of the hydrogen storage and transportation system according to the organic chemical hydride method. Besides, there is a possibility that the uniform-type platinum-loaded alumina catalyst can be widely applied to the existing catalytic reaction processes in which the platinum-loaded alumina catalyst is used, and the industrial applicability is very high.

Hereinafter, preferable embodiments of the present invention will be specifically described based on Examples and Comparative Examples.

[Carrier Preparation]

A sodium aluminate aqueous solution was instantaneously added in hot dilute sulfuric acid while being vigorously stirred to obtain an aluminum hydroxide slurry suspension (pH10). This suspension was used as seed aluminum hydroxide and while stirring was continued, an operation of alternately adding the hot dilute sulfuric acid and the sodium aluminate aqueous solution at a constant interval was repeated to obtain filtered and washed cake.

This cake was extruded and dried, and thereafter was calcined at 500° C. for 3 hours. The alumina carrier thus obtained had a BET surface area of 257 m²/g, a pore volume as measured by a mercury injection method of 0.66 cm³/g, an average pore diameter of 9.3 nm, and a sharp pore distribution in which most pores were concentrated around the average pore diameter. The volume occupied by pores with a pore diameter of 7-13 nm was 85% or more of the total pore volume, and from this result, the obtained porous γ-alumina carrier satisfied the requirements of the surface area of 150 m²/g or more, the pore volume of 0.40 cm³/g or more, the average pore diameter of 40 to 300 Å, and the pores having a pore diameter in a range of ±30 Å from the average pore diameter occupying 60% or more of the total pore volume.

Comparative Example 1 (Catalyst No. 1

For the purpose of comparison with the Examples, an egg shell-type platinum-loaded alumina catalyst (catalyst No. 1) according to Comparative Example 1 was produced. 40 mL of chloroplatinic acid aqueous solution with a concentration of 0.026 mol/L, which was prepared so that the pH value was 2.0, was added to 20 g of the porous γ-alumina carrier prepared as mentioned above, and this was left for 3 hours for impregnation before water was removed with an evaporator. Subsequently, the resultant was dried for 3 hours at 120° C. and then was calcined for 3 hours at 450° C. in a muffle furnace under air flow, whereby an egg shell-type platinum-loaded alumina catalyst on which 1 wt % of platinum was loaded (catalyst No. 1) was prepared.

Comparative Example 2 (Catalyst No. 2

40 mL of sodium (Na) nitrate aqueous solution with a concentration of 0.085 mol/L was added to 20 g of the egg shell-type platinum-loaded alumina catalyst prepared and obtained similarly to Comparative Example 1, and this was left for 3 hours for impregnation before water was removed with an evaporator. Subsequently, the resultant was dried for 3 hours at 120° C. and then was calcined for 3 hours at 450° C. in muffle furnace under air flow, whereby, an egg shell-type alkali-added platinum-loaded alumina catalyst on which 0.8 wt % of sodium (Na) and 1 wt % of platinum were loaded (catalyst No. 2) was obtained. The egg shell-type alkali-added platinum-loaded alumina catalyst according to Comparative Example 2 corresponds to the catalyst described in the aforementioned Patent Document 1.

Comparative Example 3 (Catalyst No. 3

40 mL of ammonium sulfate aqueous solution with a concentration of 0.16 mol/L was added to 20 g of the porous γ-alumina carrier prepared by the aforementioned method, and this was left for 3 hours for impregnation before water was removed with an evaporator. Subsequently, the resultant was dried for 3 hours at 120° C. and then was calcined for 3 hours at 500° C. in a muffle furnace under air flow, whereby an alumina carrier containing sulfur was obtained.

40 mL of chloroplatinic acid aqueous solution with a concentration of 0.026 mol/L, which was prepared so that pH was 2.0, was added to 20 g of the alumina carrier containing sulfur thus prepared, and after impregnation for making the loading amount of platinum after calcination be 1.0 wt %, moisture was removed with an evaporator. Subsequently, the resultant was dried for 3 hours at 120° C. and then was calcined for 3 hours at 450° C. in a muffle furnace under air flow, whereby a uniform-type sulfur-platinum-loaded alumina catalyst which contained 1.0 wt % of sulfur and on which 1.0 wt % of platinum was dispersed and loaded (catalyst No. 3) was obtained. This method conforms to the preparation method described in Example 3 of Patent Document 2.

Comparative Example 4 (Catalyst No. 4

20 g of alumina carrier containing sulfur prepared by a method similar to Comparative Example 3 (catalyst No. 3) was impregnated with 5.6 mL of dinitrodiamine platinum aqueous solution with a concentration of 0.18 mol/L so that the loading amount of platinum after calcination was 1.0 wt %, and thereafter, moisture was removed with an evaporator. Subsequently, the resultant was dried for 3 hours at 120° C. and then was calcined for 3 hours at 450° C. in a muffle furnace under air flow, whereby an egg shell-type sulfur-platinum-loaded alumina catalyst which contained 1.0 wt % of sulfur and on which 1.0 wt % of platinum was loaded in an egg shell manner was obtained.

40 mL of sodium nitrate (Na) aqueous solution with a concentration of 0.17 mol/L was added to 20 g of the egg shell-type sulfur-platinum-loaded alumina catalyst thus prepared, and this was left for 3 hours for impregnation before water was removed with an evaporator. Subsequently, the resultant was dried for 3 hours at 120° C. and then was calcined for 3 hours at 450° C. in a muffle furnace under air flow, whereby an egg shell-type alkali-added sulfur-platinum-loaded alumina catalyst on which 0.8 wt % of sodium (Na) and 1 wt % of platinum were loaded (catalyst No. 4) was obtained.

Example 1 (Catalyst No. 5

40 mL of sodium nitrate potassium aqueous solution with a concentration of 0.085 mol/L was added to 20 g of the uniform-type platinum-loaded alumina catalyst of Comparative Example 3, and this was left for 3 hours for impregnation before water was removed with an evaporator. Subsequently, the resultant was dried for 3 hours at 120° C. and then was calcined for 3 hours at 450° C. in a muffle furnace under air flow, whereby a uniform-type alkali-added sulfur-platinum-loaded alumina catalyst according to Example 1 (catalyst No. 5) was obtained. This catalyst contained 1.0 wt % of platinum and 0.4 wt % of sodium as alkali metal, calculated as elemental sodium.

Examples 2 and 3 (Catalyst Nos. 6 and 7

By using a method similar to Example 1 with varied concentrations of sodium nitrate aqueous solution added to 20 g of the uniform-type sulfur-platinum-loaded alumina catalyst of Comparative Example 3, uniform-type alkali-added sulfur-platinum-loaded alumina catalysts in which the loading amount of sodium was 0.8 wt % and 1.6 wt %, respectively (catalyst Nos. 6 and 7), were prepared.

Example 4 (Catalyst No. 8

By using a method similar to Example 1 with the solution added to 20 g of the uniform-type sulfur-platinum-loaded alumina catalyst of Comparative Example 3 changed from sodium nitrate aqueous solution to sodium chloride aqueous solution, a uniform-type alkali-added sulfur-platinumloaded alumina catalyst in which the loading amount of sodium was 0.8 wt % (catalyst No. 8) was prepared.

Example 5 (Catalyst No. 9

40 mL of aqueous solution prepared to simultaneously contain chloroplatinic acid with a concentration of 0.026 mol/L and sodium chloride with a concentration of 0.17 mol/L so that pH was 2.0 was added to 20 g of the alumina carrier containing sulfur prepared by the method same as in Comparative Example 3, and this was left for 3 hours for impregnation before water was removed with an evaporator. Subsequently, the resultant was dried for 3 hours at 120° C. and then was calcined for 3 hours at 450° C. in a muffle furnace under air flow, whereby a uniform-type alkali-added sulfur-platinum-loaded alumina catalyst according to Example 5 (catalyst No. 9) was obtained. This catalyst contained 1.0 wt % of platinum and 0.8 wt % of sodium as alkali metal, calculated as elemental sodium.

Example 6 (Catalyst No. 10

40 mL of potassium (K) nitrate aqueous solution with a concentration of 0.044 mol/L was added to 20 g of the uniform-type platinum-loaded alumina catalyst of Comparative Example 3, and this was left for 3 hours for impregnation before water was removed with an evaporator. Subsequently, the resultant was dried for 3 hours at 120° C. and then was calcined for 3 hours at 450° C. in a muffle furnace under air flow, whereby a uniform-type alkali-added sulfur-platinum-loaded alumina catalyst according to Example 6 (catalyst No. 10) was obtained. This catalyst contained 1.0 wt % of platinum and 0.34 wt % of potassium as alkali metal, calculated as elemental potassium.

Examples 7 and 8 (Catalyst Nos. 11 and 12

By using a method similar to Example 6 with varied concentrations of the potassium nitrate aqueous solution added to 20 g of the uniform-type sulfur-platinum-loaded alumina catalyst of Comparative Example 3, uniform-type alkali-added sulfur-platinum-loaded alumina catalysts in which the loading amount of potassium was 0.7 wt % and 1.4 wt %, respectively (catalyst Nos. 11, 12), were prepared.

Example 9 (Catalyst No. 13

40 mL of calcium (Ca) acetate aqueous solution with a concentration of 0.10 mol/L was added to 20 g of the uniform-type platinum-loaded alumina catalyst of Comparative Example 3, and this was left for 3 hours for impregnation before water was removed with an evaporator. Subsequently, the resultant was dried for 3 hours at 120° C. and then was calcined for 3 hours at 450° C. in a muffle furnace under air flow, whereby a uniform-type alkali-added sulfur-platinum-loaded alumina catalyst according to Example 9 (catalyst No. 13) was obtained. This catalyst contained 1.0 wt % of platinum and 0.8 wt % of calcium as alkali metal, calculated as elemental calcium.

(Accelerated Reaction Test)

Next, by using the aforementioned Comparative Examples 1 to 4 (catalyst Nos. 1 to 4) and Examples 1 to 9 (catalyst Nos. 5 to 13), a reaction test under accelerated condition (high temperature) was performed so that differences in performance and amounts of carbon precipitation were observed in a relatively short time. The reaction test was performed under accelerated condition so that differences in performance were obtained in a relatively short time. 1.3 g of each catalyst was diluted with 11.7 g of α-alumina beads and was charged in a lengthwise central part of a stainless steel reaction tube which had an inside diameter of 12.6 mm and a length of 300 mm and which was equipped with a protective tube for a thermocouple whose outer dimension was ⅛ inch in the center of the cross section of the reaction tube. Spherical α-alumina beads with a diameter of 1 mm were placed on the upper side of the catalyst as a preheating layer. Thereafter, the temperature of the catalyst layer was raised to 380° C., and pre-treatment reduction was carried out for 15 hours in a hydrogen stream. After the pre-treatment reduction finished, the catalyst layer inlet temperature was set to 400° C., the catalyst layer outlet temperature was set to 410° C., the pressure was set to 0.3 MPa, the hydrogen gas supplied for the pre-treatment reduction was stopped, and methylcyclohexane (MCH) gas evaporated by a heater was supplied to the reactor at a flow rate of 2.9 L/h (LHSV: 8 h$^{-1}$). A cooler for cooling the gas exiting from the reactor was provided at the outlet of the reaction tube, and the resultant was collected in a stainless steel container and was separated into a liquid product such as liquefied toluene (TOL) and gas such as hydrogen gas. Composition analysis was performed separately for the collected liquid product and gas by gas chromatography, and the MCH conversion rate (%) and the TOL selectivity (%) from the reaction start to 140 hours later were calculated. Also, the catalyst after the reaction test was taken out, and an amount of carbon production, which is a cause for catalyst deterioration, was measured with a carbon/sulfur analyzer.

(Catalyst Life Test)

Next, by using the aforementioned Comparative Example 3 (catalyst No. 3) and Example 2 (catalyst No. 6), a reaction test for evaluating the catalyst stability in a long time was carried out as follows. 8.5 g of each catalyst was diluted with 129 g of spherical α-alumina beads with an outer diameter of 5 mm and charged in a lengthwise central part of a stainless steel reaction tube which had an inside diameter of 21.2 mm and a length of 816 mm and which was equipped with a protection tube for a thermocouple whose outer dimension was ¼ inch in the center of the cross section of the reaction tube. Spherical α-alumina beads with an outer diameter of 1 mm were placed on the upper side of the catalyst as a preheating layer. The temperature of the catalyst layer was set to 380° C., and pre-treatment reduction was carried out for 15 hours in a hydrogen stream. After the pre-treatment reduction finished, the catalyst layer inlet temperature was set to 280° C., the catalyst layer outlet temperature was set to 380° C., the reaction pressure was set to 0.55 MPa, and MCH gas was supplied to the reactor at a flow rate of 2.8 L/h (LHSV: 2.6 h$^{-1}$). A cooler for cooling the gas exiting from the reactor was provided at the outlet of the reaction tube, and the resultant was collected in a stainless steel container and was separated into a liquid product such as liquefied toluene (TOL) and gas such as hydrogen gas. Composition analysis was performed separately for the collected liquid product and gas by gas chromatography, and the MCH conversion rate (%) and the TOL selectivity (%) from the reaction start to 1400 hours later were calculated.

The result of the aforementioned accelerated reaction test is shown in Table 1, and the result of the catalyst life test is shown in Table 2.

TABLE 1

| | | | | | accelerated test | | | | | | |
|---|---|---|---|---|---|---|---|---|---|---|---|
| | | | | | | | after 20 hours | | after 140 hours | | |
| | | | | | amount of addition of alkali metal | | MCH conversion | TOL | MCH conversion | TOL | amount of carbon |
| | catalyst No. | catalyst type | S (wt %) | Pt (wt %) | additive | (mmol/ g-carrier) | (wt %) | rate (%) | selectivity (%) | rate (%) | selectivity (%) | production (wt %) |
| 1 | Comparative Example 1 | ES | none | 1.0 | none | none | none | 95.7 | 99.3 | 90.4 | 99.6 | 2.6 |
| 2 | Comparative Example 2 | ES | none | 1.0 | NaNO$_3$ | 0.35 | 0.8 | 94.5 | 99.6 | 88.0 | 99.8 | 1.5 |
| 3 | Comparative Example 3 | uniform | 1.0 | 1.0 | none | none | none | 98.7 | 99.8 | 95.0 | 99.8 | 2.6 |
| 4 | Comparative Example 4 | ES | 1.0 | 1.0 | NaNO$_3$ | 0.35 | 0.8 | 97.3 | 98.0 | 93.9 | 97.9 | 0.5 |
| 5 | Example 1 | uniform | 1.0 | 1.0 | NaNO$_3$ | 0.17 | 0.4 | 98.9 | 99.9 | 97.6 | 99.9 | 1.2 |
| 6 | Example 2 | uniform | 1.0 | 1.0 | NaNO$_3$ | 0.35 | 0.8 | 98.5 | 99.9 | 97.2 | 99.9 | 0.7 |
| 7 | Example 3 | uniform | 1.0 | 1.0 | NaNO$_3$ | 0.70 | 1.6 | 96.1 | 99.9 | 93.9 | 99.9 | 0.7 |
| 8 | Example 4 | uniform | 1.0 | 1.0 | NaCl | 0.35 | 0.8 | 98.4 | 99.9 | 97.1 | 99.9 | 0.7 |
| 9 | Example 5 | uniform | 1.0 | 1.0 | NaCl (simultaneous) | 0.35 | 0.8 | 98.1 | 99.9 | 97.1 | 99.9 | 0.7 |
| 10 | Example 6 | uniform | 1.0 | 1.0 | KNO$_3$ | 0.08 | 0.3 | 98.8 | 99.9 | 96.6 | 99.9 | 1.3 |
| 11 | Example 7 | uniform | 1.0 | 1.0 | KNO$_3$ | 0.17 | 0.7 | 98.8 | 99.9 | 97.4 | 99.9 | 1.2 |
| 12 | Example 8 | uniform | 1.0 | 1.0 | KNO$_3$ | 0.35 | 1.4 | 97.9 | 99.9 | 96.8 | 99.9 | 0.6 |
| 13 | Example 9 | uniform | 1.0 | 1.0 | Ca acetate | 0.17 | 0.8 | 96.4 | 99.9 | 91.4 | 99.9 | 1.5 |

TABLE 2

| | | | | | | life test | | | | | |
| | | | | | | | after 50 hours | | after 1400 hours | | |
| | | | | | amount of addition of alkali metal | | MCH conversion | TOL | MCH conversion | TOL | amount of carbon |
| catalyst No. | catalyst type | S (wt %) | Pt (wt %) | additive | (mmol/ g-carrier) | (wt %) | rate (%) | selectivity (%) | rate (%) | selectivity (%) | production (wt %) |
|---|---|---|---|---|---|---|---|---|---|---|---|
| 3 Comparative Example 3 | uniform | 1.0 | 1.0 | none | none | none | 97.5 | 99.6 | 96.6 | 99.8 | 3.1 |
| 6 Example 2 | uniform | 1.0 | 1.0 | NaNO$_3$ | 0.35 | 0.8 | 97.1 | 99.9 | 96.8 | 99.9 | 1.2 |

From Table 1, it can be seen that compared to the egg shell-type platinum-loaded alumina catalyst of Comparative Example 1 (catalyst No. 1) in which platinum was dispersed and loaded on only the outer shell part of the carrier and the egg shell-type alkali-added platinum-loaded alumina catalyst of Comparative Example 2 (catalyst No. 2), the uniform-type sulfur-platinum-loaded alumina catalyst of Comparative Example 3 (catalyst No. 3) in which sulfur was dispersed and loaded over the entirety of the alumina carrier and platinum was dispersed and loaded over the entirety of the alumina carrier demonstrated a high MCH conversion rate and a high TOL selectivity both at an initial stage of the accelerated reaction test and after 140 hours of reaction (the MCH conversion rate was 98.7% and 95.0%, respectively), and thus, is excellent in the catalyst stability and selectivity.

As described above, the uniform-type sulfur-platinum-loaded alumina catalyst of Comparative Example 3 demonstrates excellent catalyst performance, but the amount of carbon production after the reaction test was 2.6 wt %, which is greater than that of the egg shell-type alkali-added platinum-loaded alumina catalyst of Comparative Example 2 (catalyst No. 2). From this result, it is inferred that in the catalyst of Comparative Example 3, dispersity is improved due to uniform dispersion of platinum, which is the catalyst component, over the carrier, and this provides numerous active sites effective for reaction, whereby even though the amount of carbon precipitation is increased, active sites effective for reaction are still held.

From Table 1, it can be seen that in Example 1, in which 0.4 wt % of sodium was added as alkali metal to the uniform-type sulfur-platinum-loaded alumina catalyst of Comparative Example 3, the MCH conversion rate at the initial stage of the accelerated reaction test was 98.9%, which was about the same as in Comparative Example 3, the MCH conversion rate after 140 hours was maintained at 97.6%, which was higher than 95.0% in Comparative Example 3, the TOL selectivity was 99.9%, which was better than that of Comparative Example 3, and the amount of carbon production after the reaction test was decreased to 1.2% or to about a half. The improvement of TOL selectivity was 0.1% numerically, but since the amount of impurities produced is calculated according to the formula below, the improvement of the TOL selectivity from 99.8% to 99.9% suppresses the amount of impurities produced to about a half.

Amount of impurities produced=Supply amount of
MCH×MCH conversion rate/100×(100−TOL
selectivity)/100

Similarly, from Table 1, it can be seen that in Example 6 also, in which 0.3 wt % of potassium was added as alkali metal to the uniform-type sulfur-platinum-loaded alumina catalyst of Comparative Example 3, the MCH conversion rate at the initial stage of the accelerated reaction test was about the same as in Comparative Example 3, the MCH conversion rate after 140 hours was maintained at 96.6%, which was higher than 95.0% in Comparative Example 3, and the amount of carbon production after the reaction test was decreased to 1.3% or to about a half.

Similarly, from Table 1, it can be seen that in Example 9 also, in which 0.8 wt % of calcium was added as alkali metal to the uniform-type sulfur-platinum-loaded alumina catalyst of Comparative Example 3, though the MCH conversion rate at the initial stage of the accelerated reaction test was 96.4%, which was slightly lower than in Comparative Example 3, the TOL selectivity was improved, and the amount of carbon production after the reaction test was decreased to 1.5% or to about a half.

Further, in Example 2 for assessing the effect of the amount of addition of sodium to the uniform-type sulfur-platinum-loaded alumina catalyst (the amount of addition of sodium was 0.8 wt %), the MCH conversion rate at the initial stage was 98.5% and the MCH conversion rate after 140 hours was 97.2%, which were slightly lower than in Example 1 but were still maintained at higher values than in Comparative Example 3, and the amount of carbon production was further decreased to 0.7 wt %.

Similarly, in Example 3 for assessing the effect of the amount of addition of sodium to the uniform-type sulfur-platinum-loaded alumina catalyst (the amount of addition sodium was 1.6 wt %), the MCH conversion rate at the initial stage was 96.1% and the MCH conversion rate after 140 hours was 93.9%, which were further lowered from those of Example 2 to about the same values as in Comparative Example 3, but the amount of carbon production was decreased to 0.7 wt %.

From the results of Examples 1-3, it is considered that the addition of sodium to the uniform-type sulfur-platinum-loaded alumina catalyst is effective in decreasing the amount of carbon production and demonstrates the effect of stabilizing the MCH conversion rate due to the decrease in the amount of carbon production. On the other hand, since the MCH conversion rates at the initial stage and after 140 hours were lowered in Example 3, it is indicated that excessive addition of sodium platinum may lower the reactivity.

Similar tendency also appeared in Examples 6-8 for assessing the effect of the amount of addition of potassium to the uniform-type sulfur-platinum-loaded alumina catalyst, and the effect of suppressing the amount of carbon production was the highest when the amount of addition of potassium was 1.4 wt %, where the amount of carbon production was 0.6 wt %, but it was also confirmed that there is a tendency that the MCH conversion rate was slightly lowered.

Further, the result of Example 4 in which the sodium raw material was changed to NaCl in the addition of sodium to the uniform-type sulfur-platinum-loaded alumina catalyst was substantially the same as that of Example 2 in which the same amount of sodium was added, and thus, it can be seen that sodium raw material has no influence.

Further, the result of Example 5 in which simultaneous loading of sodium and platinum was performed in the addition of sodium to the uniform-type sulfur-platinum-loaded alumina catalyst was substantially the same as that of Example 2 in which the same amount of sodium was added, and thus, it can be seen that simultaneous loading of platinum and sodium has substantially no influence.

In Table 1, by comparing Comparative Example 4 with Example 2, it can be seen that even when the sulfur content is the same as the sodium content, an amount of decrease of the MCH conversion rate after 140 hours is obviously smaller when the catalyst type is the uniform-type than when the catalyst type is the egg shell-type. Thus, the uniform-type platinum-loaded alumina catalyst to which sulfur and alkali metal are added has a significant difference from the egg shell-type platinum-loaded alumina catalyst to which sulfur and alkali metal are added.

From the result shown in Table 2 of the catalyst life test performed using Example 2 (catalyst No. 6, sodium 0.8 wt %), which from the accelerated test results of Examples 1 to 9, demonstrated an MCH conversion rate that was relatively high and changed stably and an amount of carbon production that was relatively small, it can be seen that in the uniform-type alkali-added sulfur-platinum-loaded alumina catalyst of Example 2 to which alkali metal was added, the MCH conversion rate decreased by only 0.3% over the period from 50 hours after the reaction start to 1400 hours after the reaction start, while in the uniform-type platinum-loaded alumina catalyst of Comparative Example 3 (catalyst No. 3), the MCH conversion rate decreased by 0.9%, and thus, the uniform-type alkali-added sulfur-platinum-loaded alumina catalyst has a longer catalyst life. Also, regarding the TOL selectivity, the uniform-type alkali-added sulfur-platinum-loaded alumina catalyst maintained 99.9% over the period from 50 hours after the reaction start to 1400 hours after the reaction start, which is higher than the TOL selectivity of the uniform-type platinum-loaded alumina catalyst of Comparative Example 3 (catalyst No. 3), and thus, it can be seen that the uniform-type alkali-added sulfur-platinum-loaded alumina catalyst is a catalyst that produces a small amount of impurities. In addition, the amount of carbon production after 1400 hours of reaction test was 1.2% in Example 2, which is smaller than 3.1% in Comparative Example 3, and thus, it was confirmed that by suppressing the amount of carbon production, an effect of enhancing the stability of the catalyst can be obtained.

INDUSTRIAL APPLICABILITY

The alkali-added uniform-type platinum-loaded alumina catalyst according to the present invention can be favorably used in the dehydrogenation reaction of hydrogenated aromatics such as methylcyclohexane used as a hydrogen energy carrier, and can contribute to practical implementation of the hydrogen storage and transportation system by organic chemical hydride method. Besides, there is a possibility that the alkali-added uniform-type platinum-loaded alumina catalyst according to the present invention can be widely applied to existing catalytic reaction processes in which the platinum-loaded alumina catalyst is used. Thus, the present invention has very high industrial applicability.

LIST OF REFERENCE NUMERALS

1 carrier
2 metal loading part

What is claimed is:

1. A method of dehydrogenating methylcyclohexane, comprising:

charging a uniform-type platinum-loaded alumina catalyst in a reaction tube;

supplying methylcyclohexane gas to the catalyst; and setting an inlet temperature of the catalyst to 280 to 400° C., an outlet temperature to 380 to 410° C., a reaction pressure to 0.3 to 0.55 MPa, and wherein the uniform-type platinum-loaded alumina catalyst consists of:

an alumina carrier;

sulfur or a sulfur compound dispersed over an entire cross section of the alumina carrier;

platinum dispersed and loaded over the entire cross section of the alumina carrier; and one or more alkali metals selected from the group consisting of sodium and potassium, wherein a content of the sulfur or the sulfur compound is 0.15 to 5.0 wt % calculated as elemental sulfur, a content of the alkali metal(s) is 0.1 to 5.0 wt % calculated as elemental alkali metal, a content of the platinum is 0.05 to 5.0 wt % calculated as elemental platinum, and the alumina carrier has a surface area of $150 \, \text{m}^2/\text{g}$ or more, a pore volume of $0.40 \, \text{cm}^3/\text{g}$ or more, and an average pore diameter of 40 to 300 Å, with pores having a pore diameter in a range of ±30 Å from the average pore diameter occupying 60% or more of a total pore volume.

* * * * *